United States Patent [19]
Reis

[11] Patent Number: 4,475,544
[45] Date of Patent: Oct. 9, 1984

[54] BONE GRIPPING FORCEPS

[76] Inventor: Norman I. Reis, 494 N. Middletown Rd., Pearl River, N.Y. 10965

[21] Appl. No.: 351,537

[22] Filed: Feb. 23, 1982

[51] Int. Cl.³ .......................... A61F 5/04; A61B 17/28
[52] U.S. Cl. .................... 128/92 EA; 128/321
[58] Field of Search ................. 128/92 EA, 92, 92 E, 128/321

[56] References Cited

U.S. PATENT DOCUMENTS

| | | | |
|---|---|---|---|
| 1,985,108 | 12/1933 | Rush | 128/346 |
| 2,111,161 | 5/1937 | Wilson | 138/321 |
| 2,583,892 | 1/1952 | Shellhouse | 128/321 |
| 2,583,896 | 1/1952 | Siebrandt | 128/92 EA X |
| 3,779,248 | 12/1973 | Karman | 128/321 |
| 3,823,719 | 7/1974 | Cummings | 128/322 |
| 4,009,712 | 3/1977 | Burstein et al. | 128/92 |
| 4,159,716 | 7/1979 | Borchers | 128/80 |
| 4,201,215 | 5/1980 | Crossett et al. | 128/335 |

OTHER PUBLICATIONS

American V. Mueller, *The Surgical Armamentarium*, 1980, p. 154.

*Primary Examiner*—Stephen C. Pellegrino
*Attorney, Agent, or Firm*—Sherman & Shalloway

[57] ABSTRACT

A bone clamp for temporarily applying compressive force to portions of bone during surgical procedures has a configuration of a forceps. The device has a pair of sharp distal ends which are turned inwardly so that the bone may be gripped between the ends. A compressive force is maintained between the distal ends by means of a ratcheting arrangement near the handles. The device may be used to hold bone fragments together while surgical procedures are performed, such as the insertion of a bone screw to a fracture site, after which the clamp is released. The distal ends are approximately collinear, thereby allowing the clamp to pivot about the distal ends out of the way of surgical procedures to be performed when the clamp is in place.

7 Claims, 4 Drawing Figures

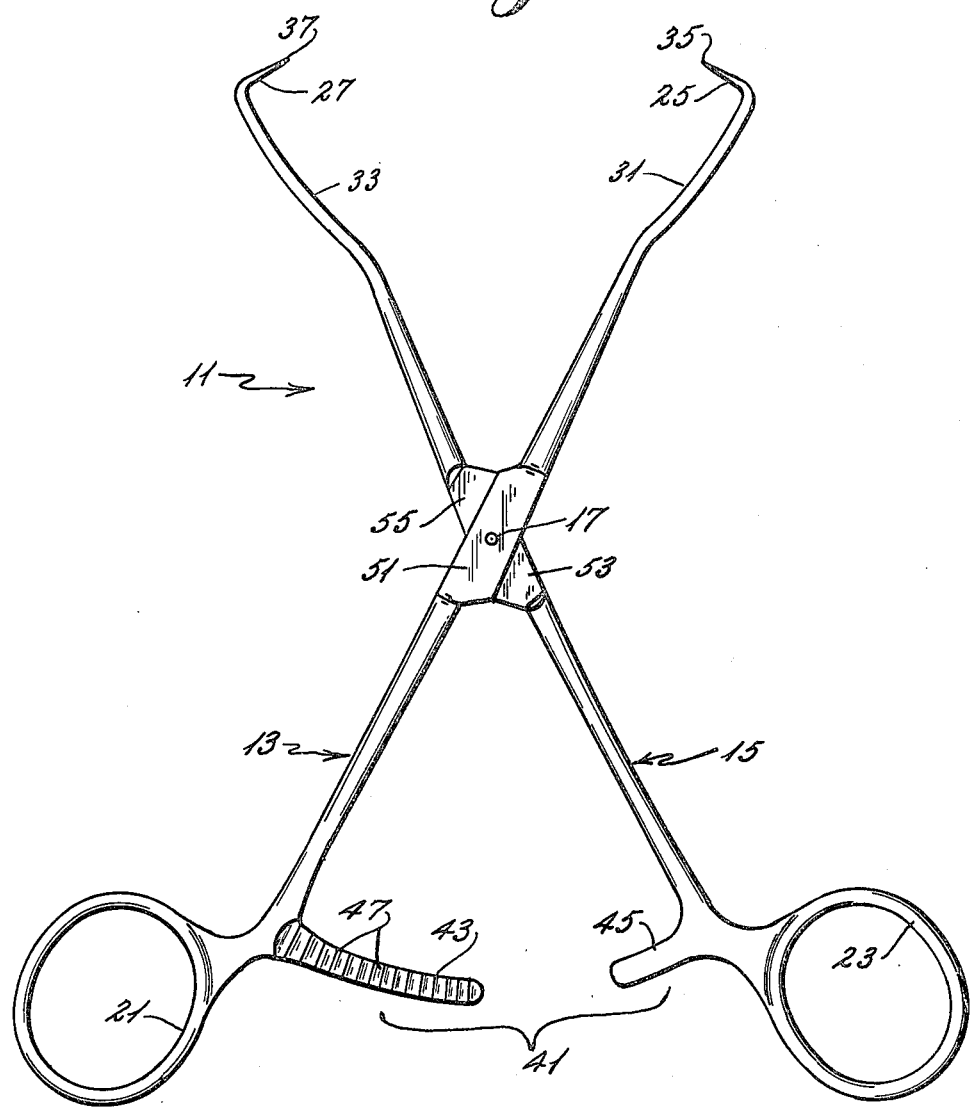
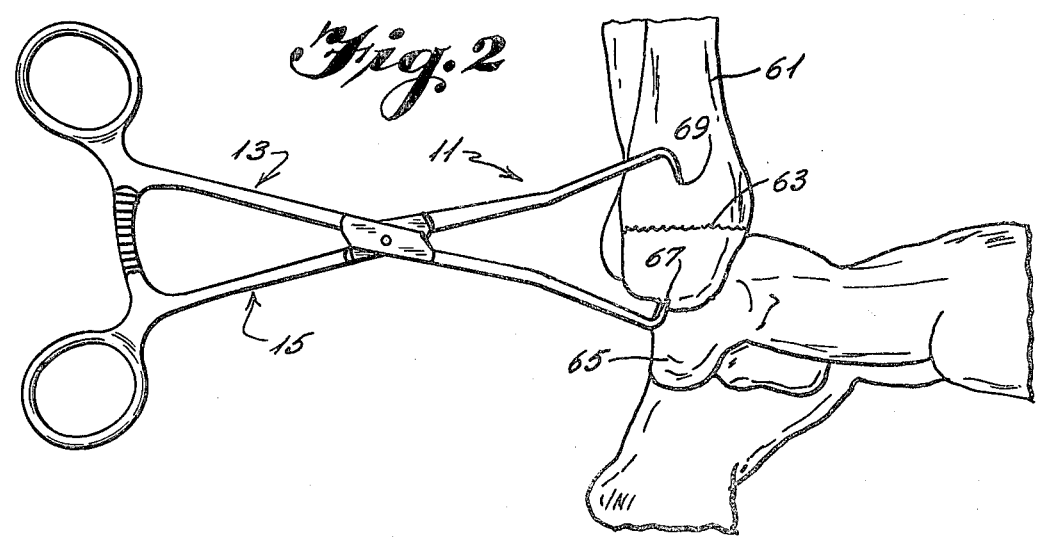

BONE GRIPPING FORCEPS

BACKGROUND OF THE INVENTION

1. Field of the Invention

This invention relates broadly to clamping devices used in orthopedic surgery and more specifically to clamps which are used temporarily during the surgery procedure and removed prior to the completion of surgery. The orthopedic surgeon frequently encounters fractures in which he desires to maintain alignment of the bone fragments by installing a screw, plate, pin or wire across the fracture. Such a plate or pin may be either temporary, to be removed after the healing of the fracture, or permanently left at the fracture site. Regardless of the specific nature of this type of repair, it is important to clamp the bone fragments together while such a plate or pin is being installed in order that the bone fragments may be maintained in alignment and in order that no gaps exist which could increase the chances of non-union. The situation would be most critical when, after a bone plate is fixed to one bone fragment, the plate is about to be fixed to a second bone fragment. Because of the downward pressure applied by the surgeon when installing a bone screw, the second bone fragment is liable to become misaligned with respect to the other bone fragment. Because of the use of bone screws, such misalignment would be difficult to correct because of the nature of the screw hole.

2. Description of the Prior Art

A number of efforts have been made in the prior art to provide bone-clamping apparatus for use during a surgical procedure. A device represented by U.S. Pat. No. 1,985,108 to Rush uses opposed curved clamping fingers to engage two sides of a bone during the insertion of a plate. This arrangement is intended to be placed around the bone in order to align the bone along its axis, as opposed to longitudinal compression. Various other clamps have been proposed which surround a fractured bone in order to provide temporary support for the bone while the bone is being repaired. One surgeon even adapted a pair of curved plate-like jaws to a pair of Vice Grips (Trademark for a type of locking jaw pliers) for the purpose of clamping fractured bones.

In addition to a Vice Grips (TM) arrangement, thumbscrew arrangements and ratcheting handles have been used to hold the bone clamps in a clamping position. An example of a thumbscrew arrangement is shown in the above-mentioned Rush patent. A ratcheting arrangement is exemplified by U.S. Pat. No. 4,009,712 to Burstein, et al.

The use of inwardly-turned ends for effecting bone clamping is known. For example, U.S. Pat. No. 4,201,215, to Crossett, et al., shows the use of inwardly-turned ends.

In the prior art it was usually necessary to provide clearance around a temporary clamp in order to perform surgical procedures, such as screwing on a bone plate. In cases, such as when using the above-mentioned Rush patent, where a bone plate is either held in position or where the position of the bone plate is closely determined by the position of the clamp, the clamp could be constructed so as to clear a specified path for the surgeon, such as when a screwdriver was used to insert bone screws. In any case, most of the prior art apparatus provided for surgical access by having handles which, when the clamp was inserted onto a bone, were hopefully out of the way of surgical procedures.

Additionally, most of the prior art bone clamps required a substantial area of the bone to be exposed. This is particularly true in cases where curvate plate-like jaws wrap around a bone. If the fracture site happens to occur in the vicinity of the nutrient artery or at a similar critical location, extreme care must be taken to avoid damaging the tissue at this area. This can present a problem when the nutrient artery is located behind an incision site and must be avoided as the bone is exposed from behind.

In many cases, the fracture site occurs at the end of a long bone, such as the end of the tibia or ulna or in one of the short irregular bones. In such cases, it may be difficult to grip both sides of the fracture with a bone clamp which is designed to surround the shaft of a long bone, in part because of the more irregular shape of the bone at this area.

SUMMARY

It is, accordingly, an object of the present invention to provide a surgical bone clamp which may be pivoted out of the way during surgery while still maintaining its clamping force to the bone. It is a further object to provide a bone clamp which may be applied to the ends of various bones in order to provide a compressive force without reaching around the bone and which can apply the force more-or-less parallel to the longitudinal axis of the bone. It is a further object to provide a bone clamp which may be used to apply clamping force to a large variety of bones, having a variety of contours at the fracture site. It is a further object to provide a bone clamp which is simple to apply to the bone in that the amount of incision necessary to expose bone to apply the clamp is minimized and in that the actual clamping operation is performed simply and easily. It is a further object to provide a bone-clamping apparatus in which the bone-clamping procedure is performed within full view of the surgeon.

Accordingly, in one aspect of the invention, an apparatus is provided which has the configuration of a forceps and which has distal ends which are turned inwardly towards each other so that the distal ends are nearly collinear when the apparatus is being used as a bone clamp. The distal ends have sharp points which engage the bone to enable clamping pressure to be applied between them. A ratcheting mechanism is provided near the proxmal end of the apparatus so that the clamping force can be maintained. With this arrangement, two segments of a fractured bone may be clamped together by a surgeon and the surgeon may then permit the bone clamp to pivot about the distal ends so that the proxmal ends of the bone clamp is clear of the surgical site. In this manner, a further procedure, such as the attachment of a bone plate or a pin may be performed while the bone fragments are clamped together. This arrangement also provides the surgeon with an ability to repair comminuted fractures, in which a first portion of the fracture may be secured by the bone clamp and fixed with a plate and then an additional portion of the fracture may then be secured by possibly the same bone clamp to be fixed to the previously-mentioned portion. With a pair of such bone clamps, the entire fracture can be clamped.

Wide fractures can also be repaired using a pair of clamps by applying a clamp at each end of the fracture.

In a further aspect of the invention, a bone clamp is provided for engaging bone segments between distal ends of the clamp which are pointed toward one another, in which the bone clamp is ratcheted at a proximal end and has a flexibility which enables a resilient force to be applied to the bone segments while at the same time permitting that force to be applied throughout the range of ratcheting.

In a further aspect of the invention, a method is presented for repairing bone fractures in which the bone fractures are first aligned and a bone clamp is attached to the bone so that one of a pair of distal ends of the bone clamp is applied to one segment of the bone while the other distal end is applied to another segment of the fractured bone. The segments are aligned and clamping force is applied to the clamp by drawing together a pair of arms extending from the distal ends against a ratchet. The clamp is permitted to pivot about an axis defined by the distal ends with the ratcheting mechanism maintaining a compressive force between the segments. At this time, surgical fixation of the bone segments may be performed and the bone clamp may then be released by releasing the ratcheting mechanism.

BRIEF DESCRIPTION OF THE DRAWINGS

FIG. 1 shows a bone clamp in accordance with a preferred embodiment of the present invention.

FIG. 2 shows the bone clamp of FIG. 1 being applied to a fracture occurring at the medial malleous of the distal end of the tibia bone.

DESCRIPTION OF THE PREFERRED EMBODIMENT

Figure 3:
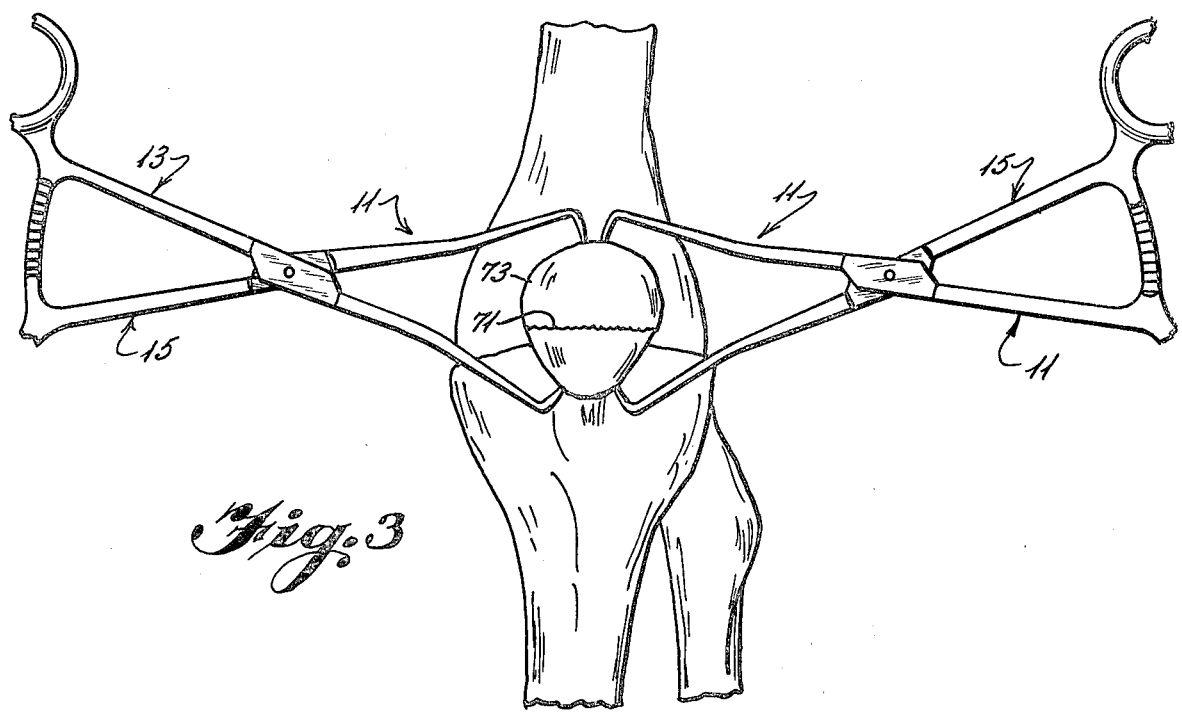
FIG. 3 shows a pair of bone clamps of FIG. 1 being applied to a fracture occurring at the patella (kneecap).

Referring to FIG. 1, a bone clamp according to a preferred embodiment of the invention is shown. As can be seen from that figure, the clamp 11 is constructed about a pair of longitudinal scissors arms 13, 15 which intersect at a pivot bearing 17. Scissors arm 13 will be referred to as the first scissor arm and scissors arm 15 will be referred to as the second scissor arm. The scissors arms 13, 15 each have, at the proximal ends thereof, first and second finger grips 21, 23, respectively.

The pivot bearing 17 forms an axis of rotation of the relative movement between the first and second scissors arms 13, 15 so that the scissors arms can pivot in a normal scissors or forceps fashion. The pivot bearing is formed as a flanged shaft which is fixedly inserted into the first scissors arm 13 and through which the second scissors arm 15 passes in a manner wellknown in the art of scissors making. While not shown in detail, typically this comprises a screw with a short head which forms a flange and a shank which is equivalent in length to the thickness of the first scissors arm 13 at the location of the pivot bearing, as recessed at the location of the pivot bearing 17. The clamp 11 is closed, as with scissors, by bringing the finger grips 21, 23 together in a conventional fashion. This also brings the distal ends portions 25, 27 together.

The distal end portions 25, 27 are turned inwardly toward each other and therefore each is arranged generally perpendicular to the length of its respective scissors arm 13 or 15. This arrangement permits the distal end portions to be generally parallel at one portion of the relative movement of the first or second scissors arm 13, 15. The distal end portions are each also located an equal distance from the pivot bearing 17, thus resulting in the distal end portions 25, 27 being approximately collinear when they are approximately parallel.

In order that the distal end portions 25, 27 do not engage each other when the clamp 11 is closed, the scissors arms 13, 15 each has an intermediate end part 31, 33, respectively. The intermediate end parts 31, 33 bend outwardly from each other so that when the clamp 11 is closed, there is an increasing gap between the first and second scissors arms, with the increasing gap occurring as the intermediate end parts 31, 33 approach the distal end portions 25, 27. The intermediate end parts 31, 33 each being at a distance approximately midway to 2/3 way from the pivot bearing 17 to the distal end portions 25, 27 and the intermediate end parts 31, 33 each terminate with their associated distal end portions 25 or 27. Therefore, following the first scissors arm 13 from the pivot bearing distally, the first scissors arm 13 begins to bend outwardly from the second scissor arm 15 along intermediate end part 31 and continues to spread until the scissors arm 13 turns inwardly at the first distal end portion 25. The second scissors arm 15 has a similar construction.

The distal end portions 25, 27 terminate in first and second distal points 35, 37, respectively, which are formed as sharp points.

Immediately distal of the first and second finger grips 21, 23, is a ratcheting mechanism 41. The ratcheting mechanism 41 comprises a ratchet arm 43 mounted on the first scissors arm 13 and a ratchet catch 45 mounted on the second scissors arm 15, with the ratchet arm 43 and ratchet catch 45 in an engaging relationship. The ratchet arm 33 and catch 45 will engage each other so as to prevent the finger grips from separating until such time as a surgeon or other person applies a twisting movement more-or-less parallel to the axis of the pivot bearing 17 in order to lift the ratchet catch 45 away from the ratchet arm 43. This prevents the distal points 35, 37 from inadvertently separating from each other by causing the scissors arms 13, 15 to freely pivot about the pivot bearing 17.

The ratchet arm 43, being formed in a conventional fashion, comprises a plurality of individual ratchet teeth 47 against which the ratchet catch 45 engage. As is well known, successive ratchet teeth 47, are separated from each other by a more-or-less fixed linear distance. For this reason, the ratchet can only engage the ratchet arm at a number of positions roughly equal to the number of individual ratchet teeth 47. It is desirable to be able to lock the scissors arms 13, 15 with the distal points 35, 37 anywhere within a given range of distances from each other, thereby giving the distal end an "infinite" adjustability within that range. The scissors arms 13, 15 are therefore constructed to have a flexibility which is sufficient to allow such "infinite" adjustability of the distal points whenever pressure is maintained throughout the range of the ratchet mechanism 41.

In order to stabilize the scissors arms 13, 15 laterally with respect to one another, particularly when the ratcheting mechanism is being engaged or disengaged, the scissors arms 13, 15 are each provided with a crossover section 51, 53, respectively, which is machined so that the scissors arms 13, 15 cross each other along a planar interface 55. The planar interface 55 is perpendicular to the pivot bearing 17 and cooperates with the pivot bearing 17 to establish the direction of relative movement between the scissors arms 13, 15. Thus, when the ratcheting mechanism 41 is being operated, causing the scissors arms 13, 15 to flex between the pivot bearing 17 and the ratcheting mechanism 41, a minimum of twisting occurs at the distal end portions 25, 27.

The planar interface 55 is arranged so that the release of the ratcheting mechanism 41 must occur by a twisting movement against the planar interface 55. As can be seen from FIG. 1, the crossover section 51 associated with the first scissors arm 13 has its crossover section 51 facing downward against the interface 55 as viewed in that figure. The ratchet arm 43 has its teeth 47 facing upward in that view. Likewise, the second scissors arm 15 has its crossover section 53 facing upward against the interface 55 (or crossover section 51), whereas the ratchet catch 45 faces downward. This causes force applied to separate the ratchet arm from the ratchet catch to act against the interface 55 proximally of the pivot bearing 17, thus stabilizing the clamp 11 when the ratcheting mechanism 41 is being operated.

In order to apply a tension between the distal points 35, 37 which is transferred to the ratcheting mechanism 41, the scissors arms 13, 15 are made flexible, particularly between the ratcheting mechanism 41 and the pivot bearing 17 and between the pivot bearing 17 and the distal end portions 25, 27. An appropriate flexible material is ordinary surgical stainless steel which is austenitic or otherwise resistant to autoclaving and which has a sufficient elastic range to permit the desired flexibility without permanently deforming. This flexibility, particularly between the pivot bearing 17 and the ratcheting mechanism 41, permits the ratchet catch 45 to be separated from the ratchet arm 43.

OPERATING PROCEDURES

Referring to FIG. 2, the bone clamp 11 is being used in a repair of the medial malleolus (which is the distal extremity of the tibia bone 61). The tibia 61 has a fracture 63 which, as is typical, occurs transverse to the length of the bone 61. As can be seen, the first distal point 35 is engaging the end of the bone located distally of the fracture and the second distal point 37 is engaging the bone proximally of the fracture. In order to effect a permanent repair of a bone such as the tibia 61, an incision is first made into the soft tissue (not shown) surrounding the tibia 61 in order to expose the fracture site. If necessary, astragulus 65 is pivoted so as to provide access to the distal end of the tibia 61, as the surgeon sees fit. The surgeon then selects a pair of pressure points 67, 69 on the external surface of the bone 61. The pressure points 67, 69 are selected to establish a line of compression along which alignment of the tibia 61 can be maintained across the fracture 64. In the case of partial fractures (assuming a partial fixation repair is to be made, the nonsegmented portion of the bone can be relied upon to provide partial alignment support and the application of compressive force across the fracture will usually align the bone. In the case of the complete fracture, shown, the pressure points 67, 69 must be carefully selected in order that the bone 61 is maintained in proper alignment in all directions across the fracture 63. Because of the irregular shape of the fracture 63, the bone 61 will help to maintain the alignment to some degree in either case.

When the pressure points 67, 69 are selected, the pressure points 67, 69 are used as purchase sites for engagement by the distal points 35, 37, respectively. An initial inward pressure is applied to cause the distal points 35, 37 to engage the tibia 61 by first drawing the finger grips 21, 23 together. If the tibia 61 is not properly aligned across the fracture 63, the finger grips 21, 23 are at that time slightly drawn apart while releasing the ratchet 41. The tibia 61 is then placed in alignment. With the tibia 61 in alignment, the finger grips 21, 23 are again brought together. If the tibia 61 remains aligned, a bone screw (now shown), bone pin (also not shown) or other bone fixation device is applied to the bone at that time. If alignment of the bone with the permanent or semi-permanent fixation device is to be established by drilling, the drilling is accomplished and the clamp 11 may remain in place until after the fixation device is applied.

It is possible to install a permanent or semi-permanent fixation device on the bone 61 on one side of the fracture 63, prior to aligning the bone 61. In this case, the alignment is made in a manner similar to that described above, but with the permanent or semi-permanent fixation device partially installed as stated. Because the distal end portions 25, 27 are approximately collinear at least to the extent that the distal points 35, 37 point toward one another, it is possible to allow the clamp 11 to swing from an axis passing through the pressure points 67, 69 and out of the way of the remaining surgery. For this reason, it is not necessary to provide a special offset or a special provision for the clamp 11 to remain clear of the remaining surgery.

An additional advantage is provided by the direction of force being applied by the clamp 11. This also results from the fact that the distal end portions 25, 27 are approximately collinear and extend outwardly from each other away from the distal points 35, 37. Therefore, the distal points 35, 37 are often the part of the clamp 11 which is closest to the fracture site. This means that the clamp 11 according to this invention is able to be maintained in place while the permanent or semi-permanent fixation device is being installed and without interferring with the installation.

After the permanent or semi-permanent fixation device is installed, the clamp 11 is released.

FIG. 3 shows a pair of clamps 11 being used to repair a fracture 71 of the patella (kneecap) 73. In this case, a clamp is applied to each side of the fracture 71. The stabilized patella 71 can then be wired together with surgical wire (not shown) in a manner well-known to orthopedic surgeons.

Figure 4:
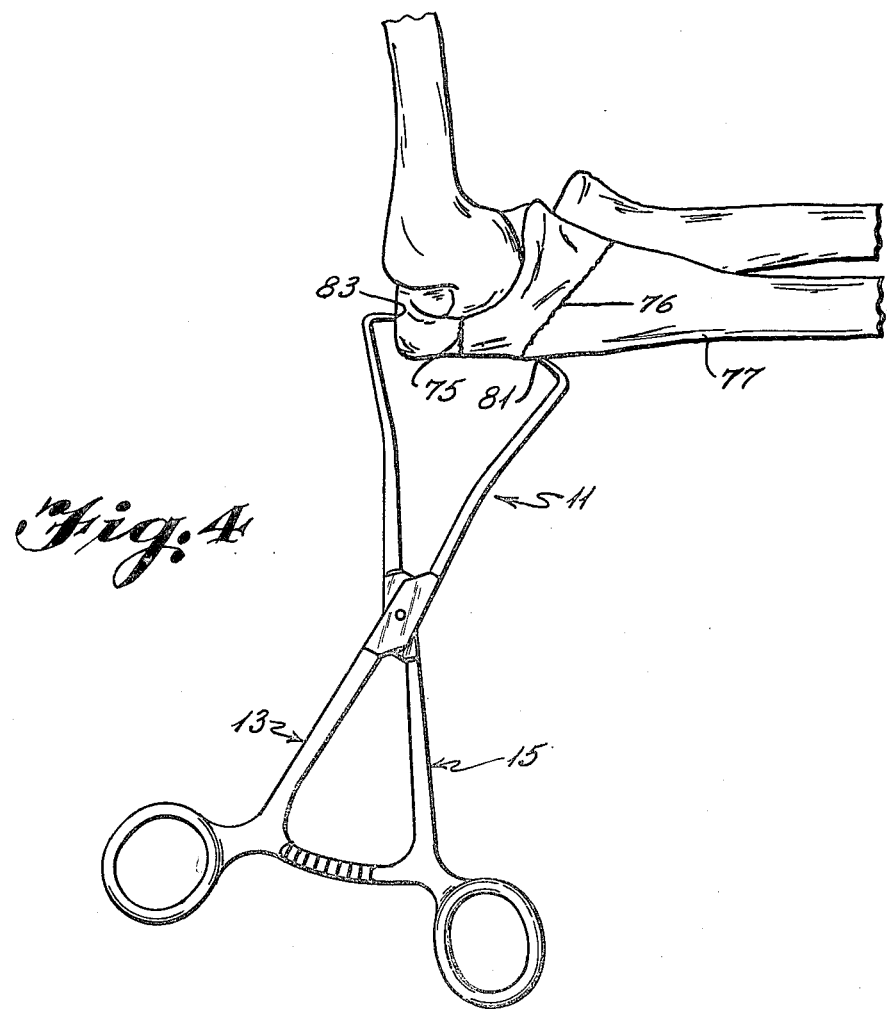
FIG. 4 shows a bone clap of FIG. 1 being applied to a comminuted fracture occurring at the olecranon of the ulnus.

FIG. 4 shows a bone clamp 11 being used in the repair of a comminuted fracture 75, 76 occurring at the olecranon of the ulna 77. As shown in this case, it is ofter possible to use a single pair of pressure points across the plural lines of fracture 75, 76. This enables the repair to be completed while using a single pair of pressure points 81, 83. On the other hand, there may be cases where alignment of bone may be difficult across plural fractures. In this case, one of the pressure points is placed between two fractures and a repair is then made across that fracture. After the repair to the first fracture is made, the bone is aligned across the second fracture and the repair is made in a similar manner.

It is anticipated that, despite the range of separation between the distal end portions afforded by the length of the scissors arms 13, 15 and the length of the ratchet arm 43, a variety of sizes of the bone clamp 11 may be provided. It is further anticipated that a number of modifications may be made to the present invention without departing from the inventive concept therein. For example, it is possible to substitute a flat or cradlelike end (not shown) for one of the distal end portions 25 or 27 while retaining the other distal end portion approximately in its present form. It is also possible to provide different proportions for the lengths of the scissors arms, intermediate end parts and distal end portions, as well as for the relative position of the pivot bearing then as shown herein. It is likewise possible to re-locate the ratchet and ratchet catch provided that the function described here remains as stated. For this reason, various modifications to the preferred embodiment may be made within the scope of the present invention.

I claim:

1. A bone clamp having a configuration of a forceps, comprising:
   (a) first and second elongate arms having a pivot bearing in a scissors fashion and each arm having a longitudinal length;
   (b) first and second finger grips at a proximal end of each of the first and second arms;
   (c) a ratcheting mechanism consisting of a ratchet on the first arm adjacent to the first finger grip, and
   (d) a ratchet grip on the second arm engageable against the ratchet as the finger grips are brought toward one another;
   (e) bone-gripping portions of the first and second arms, each bone-gripping portion consisting of:
      (1) terminal distal end parts which are turned inwardly to approximately 90° from said length to be collinear at at least one point within a range of engagement of the ratchet grip against the ratchet,
      (2) an intermediate part of the bone-gripping portion on each forceps arm connecting the proximal end part with the remainder of the arm to separate the terminal distal ends, the separation being accomplished by the arms bending outwardly away from each other at the intermediate part, said intermediate bending occurring at about midway between said pivot bearing and said terminal distal end parts with the intermediate part of each said arm forming a continuous curve with a respective said bending until terminating at said terminal distal end parts, and
      (3) a means to grip cortical bone tissue consisting of pointed ends provided on the distal ends portions, the means to grip permitting the bone clamp to pivot about the axis passing through pointed ends when bone tissue is being gripped in said manner; and
   (f) a flexing property to the arms between the terminal distal end parts and the finger grips sufficient to maintain a biasing force between the terminal distal ends throughout said range of engagement.

2. The bone clamp of claim 1 wherein the finger grips comprise closed loops which extend outwardly away from said lengths and arranged so that an opposed finger force parallel to an axis located at the pivot bearing about the arms pivot releases the ratchet from the ratchet grip.

3. The bone clamp of claim 2 wherein the ratcheting mechanism is distal of the finger grips and the arms exhibit said flexing property between the ratcheting mechanism and the distal end parts.

4. The bone clamp of claim 1 wherein the arms bend outwardly away from each other at the intermediate part to an extent necessary to maintain the terminal distal end points separated from one another.

5. The bone clamp of claim 4 wherein the point where the distal end parts are collinear is approximately midway within said range of engagement.

6. In a bone clamp having a configuration of a forceps, comprising:
   (a) first and second elongate arms having a pivot bearing in a scissors fashion and each arm having a longitudinal length;
   (b) first and second finger grips at a proximal end of each of the first and second arms;
   (c) a ratcheting mechanism consisting of a ratchet on the first arm adjacent to the first finger grip, and
   (d) a ratchet grip on the second arm engageable against the ratchet as the finger grips are brought toward one another;
   (e) bone-gripping portions of the first and second arms, each bone-gripping portion consisting of:
      (1) terminal distal and parts which are turned inwardly to approximately 90° from said length to be collinear at at least one point within a range of engagement of the ratchet grip against the ratchet,
      (2) an intermediate part of the bone-gripping portion on each forceps arm connecting the proximal end part with the remainder of the arm to separate the terminal distal ends, the separation being accomplished by the arms bending outwardly away from each other at the intermediate part, said intermediate bending occurring at about midway between said pivot bearing and said terminal distal end parts with the intermediate part of each said arm forming a continuous curve with a respective said bending until terminating at said terminal distal end parts, and
      (3) a means to grip cortical bone tissue consisting of pointed ends provided on the distal ends portions, the means to grip permitting the bone clamp to pivot about the axis passing through pointed ends when bone tissue is being gripped in said manner, and
   (f) a flexing property to the arms between the terminal distal end parts and the finger grips sufficient to maintain a biasing force between the terminal distal ends throughout said range of engagement, a method for repairing bone fractures using said bone clamp comprising:
      (a) aligning segments of the fractured bone;
      (b) holding the fractured bone in alignment with the bone clamp while fixing a long-term bone-splinting device to the bone; and
      (c) releasing the bone clamp.

7. A method for repairing a bone at a fracture site comprising:
   (a) exposing the bone across the fracture site;
   (b) selecting a pair of pressure points located on opposite segments of the fractured bone, the pair being selected to permit access of a surgical tool to each of the points and to permit a compressive force applied between the points to reduce the fracture;
   (c) applying a clamping means to the bone at the pressure points, the clamp having a pair of pointed distal end portions, each formed on the end of an intermediate portion of said clamping means which bends away from proximal portions thereof, which are aligned to point toward one another and the clamp having a means to releasably apply a compressive force between the distal end portions, the clamp being applied so that the points of the distal end portions engage the pressure points;
   (d) effecting at least a semi-permanent repair to the bone while the clamping means is applied; and
   (e) releasing the clamping means.

* * * * *